(12) United States Patent
Zelenka et al.

(10) Patent No.: US 8,167,809 B2
(45) Date of Patent: May 1, 2012

(54) IMAGING PROBE HOUSING WITH FLUID FLUSHING

(75) Inventors: Robert Zelenka, Milpitas, CA (US); Thomas C. Moore, Livermore, CA (US)

(73) Assignee: Silicon Valley Medical Instruments, Inc., Fremont, CA (US)

( * ) Notice: Subject to any disclaimer, the term of this patent is extended or adjusted under 35 U.S.C. 154(b) by 549 days.

(21) Appl. No.: 12/330,308

(22) Filed: Dec. 8, 2008

(65) Prior Publication Data
US 2009/0177093 A1    Jul. 9, 2009

Related U.S. Application Data

(60) Provisional application No. 61/008,725, filed on Dec. 20, 2007.

(51) Int. Cl.
*A61B 8/00* (2006.01)
(52) U.S. Cl. ........................ 600/462; 600/459
(58) Field of Classification Search .................. 600/459, 600/462
See application file for complete search history.

(56) References Cited

U.S. PATENT DOCUMENTS

| 5,762,066 A * | 6/1998 | Law et al. .................... 600/439 |
| 2005/0203396 A1 | 9/2005 | Angelsen et al. |
| 2007/0167824 A1 | 7/2007 | Lee et al. |

FOREIGN PATENT DOCUMENTS

| JP | 3571939 | 6/2000 |
| WO | 92-21965 A1 | 12/1992 |

OTHER PUBLICATIONS

International Search Report, for International application No. PCT/US2008/087209, dated Jul. 28, 2009.

* cited by examiner

*Primary Examiner* — Tse Chen
*Assistant Examiner* — Peter Luong
(74) *Attorney, Agent, or Firm* — Richard O. Gray, Jr.; Graybeal Jackson LLP

(57) ABSTRACT

An imaging probe for use in a catheter for ultrasonic imaging is provided. The catheter may be of the type including a sheath having an opening at a distal end for conducting a fluid there through. The imaging probe includes a distal housing coupled to a drive shaft for rotation, a transducer within the distal housing for generating and sensing ultrasonic waves, and a fluid flow promoter that promotes flow of the fluid within the sheath across the transducer.

10 Claims, 2 Drawing Sheets

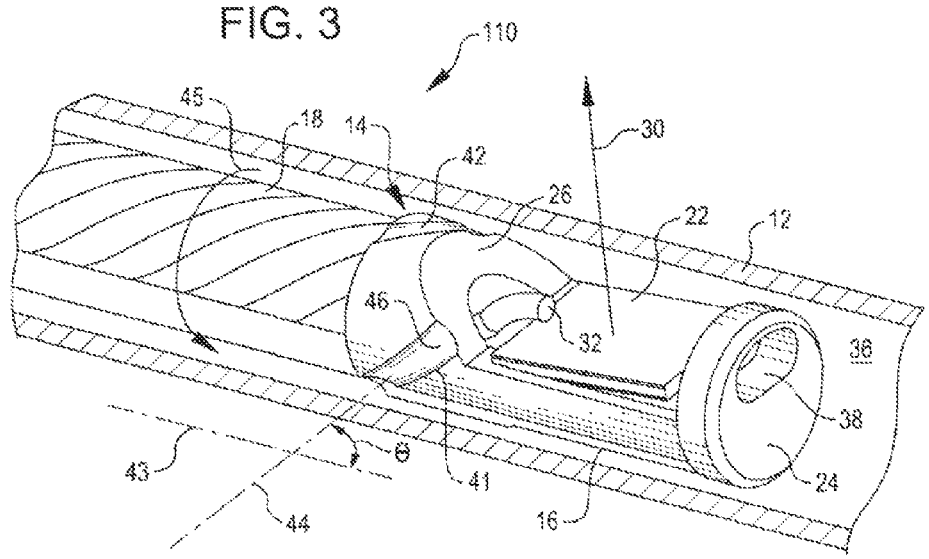

IMAGING PROBE HOUSING WITH FLUID FLUSHING

PRIORITY CLAIM

The present application claims the benefit of copending U.S. Provisional Patent Application Ser. No. 61/008,725, filed Dec. 20, 2007, which application is incorporated herein by reference in its entirety.

BACKGROUND

The present invention generally relates to an imaging probe of an imaging catheter. The present invention more specifically relates to mechanically scanned imaging probes for use in, for example, an intravascular ultrasound (IVUS) or intracardiac echo-cardiography (ICE) catheter. The present invention still further relates to such an imaging probe wherein the imaging probe is configured to assure efficient and complete fluid flushing from the catheter sheath to preclude formation of air bubbles in the vicinity of the ultrasonic transducer of the imaging probe. In addition this invention relates to imaging probe configuration to ensure the prevention of air bubbles during rotational operation by continuously directing fluid across the imaging probes transmission surface.

IVUS catheters enable the imaging of internal structures in the body. ICE catheters enable the imaging of larger internal structures in the body. Coronary IVUS catheters are used in the small arteries of the heart to visualize coronary artery disease, for example. Coronary ICE catheters are used in the cavity of the heart to visualize structural heart disease, including atrial septal defects (ASD), patent foramen ovale (PFO) and to guide various procedures including septal puctures, percutaneous valvular replacement, and various ablations treatment strategies. To that end, an IVUS or an ICE catheter will employ at least one ultrasonic transducer that creates pressure waves to enable visualization. At least one transducer is usually housed within a surrounding sheath or catheter member and rotated to enable 360 degree visualization. Because air is not an efficient medium for the transmission of the ultrasonic waves produced by at least one transducer, a fluid interface between the transducer and the sheath in which it is disposed is usually provided. Unfortunately, current imaging probe configurations do not always prevent the formation of air bubbles in the fluid in the vicinity of the transducer resulting in compromised performance of the imaging catheter. The present invention addresses this and other issues.

SUMMARY

The invention provides an imaging probe for use in a catheter for ultrasonic imaging. The catheter may include a sheath having an opening at a distal end for conducting a fluid there through. The imaging probe comprises a distal housing coupled to a drive shaft for rotation, a transducer within the distal housing for generating and sensing ultrasonic waves, and a fluid flow promoter that promotes flow of the fluid within the sheath across the transducer.

The imaging probe may further include a wall distal to the transducer and the fluid flow promoter may include an opening within the wall and adjacent to the transducer. The distal housing preferably has a first profile at a proximal end of the distal housing, a second profile at the wall distal to the transducer, and the fluid flow promoter includes the second profile being greater than the first profile to promote fluid flow over the transducer and through the opening within the wall.

The catheter has a center axis and the fluid flow promoter may further include a mounting for the transducer that disposes the transducer at an angle sloping toward the catheter center axis in a proximal direction.

The distal housing has a proximal extent and the fluid flow promoter may include at least one aqua duct within the proximal extent of the distal housing. The at least one aqua duct is preferably formed within the proximal extent of the distal housing at an angle to the center axis. The at least one aqua duct may comprise at least two aqua ducts. The transducer includes a face surface. The at least two aqua ducts may include a first aqua duct that directs fluid directly onto the face surface of the transducer and a second aqua duct that directs fluid onto the face surface of the transducer from a side of the transducer. The at least one aqua duct has a proximal side and a distal side and may be formed so that the proximal side leads the distal side in the direction of rotation of the distal housing. The at least one aqua duct may include a radius of curvature.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 3 is a perspective view showing another imaging probe embodying the invention connected to a drive cable of an intravascular ultrasound (IVUS) catheter.

DETAILED DESCRIPTION

Figure 1:
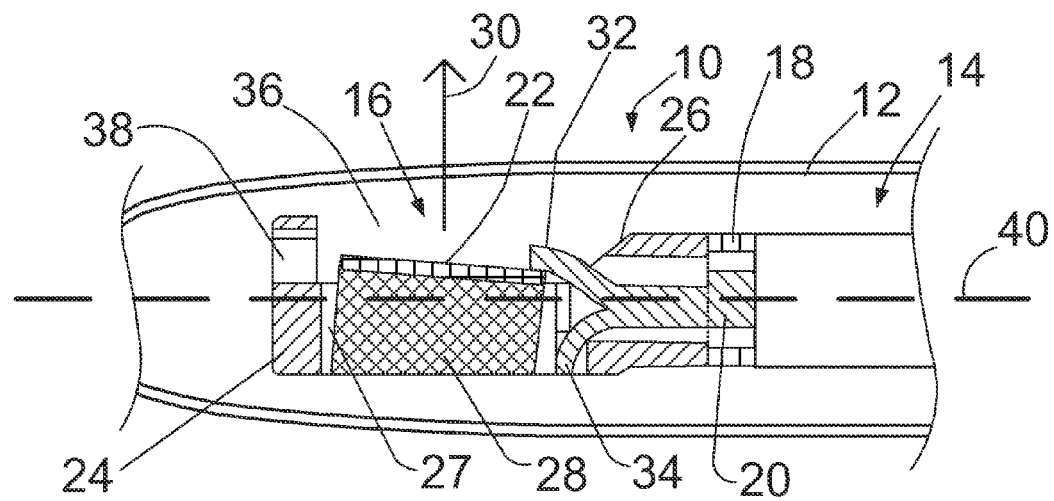
FIG. 1 is a side view, partly in section, of an ultrasonic imaging catheter in accordance with a first embodiment of the invention.

FIG. 1 shows an imaging catheter 10 with the first embodiment of the present invention. The imaging catheter 10 is particularly adapted for use as an IVUS catheter, but those skilled in the art will appreciate that the invention may be used in many other forms of ultrasound catheters as well without departing from the present invention. The catheter 10 generally includes a sheath or catheter member 12 and an imaging probe 14. As shown, the imaging probe 14 is disposed within the sheath 14. The imaging probe 14 is moveable axially within the sheath 12 to enable the sheath to remain stationary as the imaging probe is moved to scan the internal body structures to be visualized. Also, as well known, the imaging probe 14 is also rotatable to enable 360 degree scanning.

The imaging probe 14 generally includes a distal housing 16, a flexible drive shaft 18, and a coaxial cable 20. The distal housing 16 is carried on the distal end of the flexible drive shaft 18 in a known manner. The drive shaft 18 may be formed, for example, by winding multiple strands of metal wire on a mandrel to create a long spring containing a repeating series of concentric rings, or windings, of the wire. Two or more springs may be wound, one over the other, with adjacent springs being wound in opposite directions to each other. This provides a drive shaft that is both flexible and with high torsional stiffness.

The distal housing 16 generally includes the ultrasound transducer 22, a distal tip wall 24, and a proximal cutout surface 26. The transducer 22 is mounted on a transducer backing 28. The backing 28 and the distal tip wall 24 are adhered together by a conductive adhesive 27. The backing 28 is dimensioned and of such a material as to absorb ultrasonic waves from the backside of the transducer 22 so that only energy from the front side of the transducer is emitted from the imaging probe 14 in the general direction indicated by reference character 30 transverse to the exposed surface of the transducer 22. The coaxial cable 20 extends down the drive shaft 18 and includes a center conductor 32 and a shield lead 34. The center conductor 32 and shield lead 34 are coupled across the transducer 20 as shown. The coaxial cable 20 couples energy to the transducer to cause the transducer 22 to generate a pressure wave into the lumen 36 of the sheath 12. The interior of the lumen 36 is preferably filled with a fluid, such as saline. The saline flows from the proximal end of the catheter 10 to the distal end of the catheter 10 and serves to efficiently couple the ultrasonic energy into the sheath and then to the body. To support the fluid flow, the sheath includes a point of egress (not shown) for the fluid at its distal end. As previously mentioned, it is important to prevent air bubbles from being formed or residing in the vicinity of the transducer 22.

Figure 2:
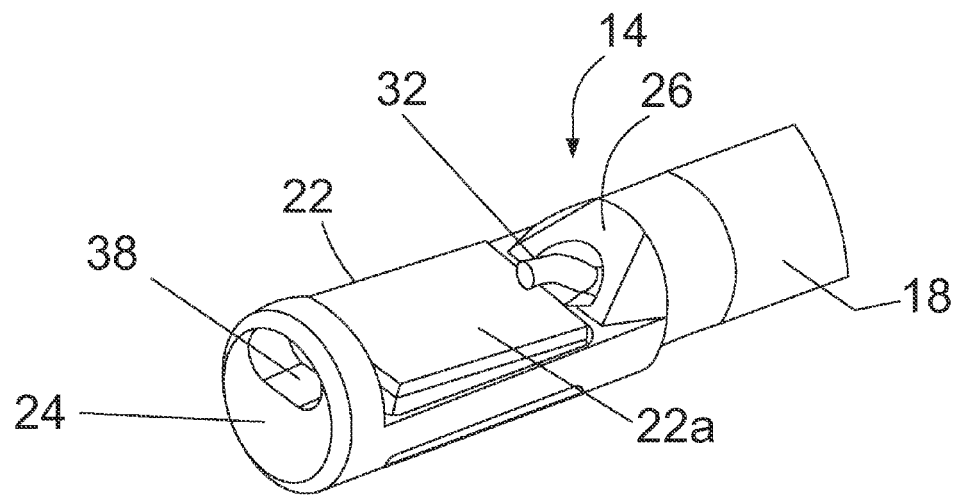
FIG. 2 is a partial perspective view of the imaging probe of the catheter of FIG. 1.

To assure that air bubble formation in the vicinity of the transducer 22 is prevented, and with additional reference to FIG. 2, the distal extent of the distal housing 16 includes a distal tip wall 24 distal and adjacent to the transducer 22. The distal tip wall 24 has an opening 38 therein adjacent to the transducer 22. Proximal to the transducer 22, the distal housing 16 has a proximal cutout forming a tapered surface 26 leading toward the transducer 22. Fluid flow within the sheath from proximal to the transducer 22 to distal of the transducer 22 is conducted down the tapered cutout surface 26, over the transducer 22, and out the distal tip wall opening 38 in a continuous manner, without turbulence, to prevent air bubble formation in the vicinity of the transducer.

The distal housing 16 at the proximal extent of the tapered cutout surface 26 has or defines a first profile substantially transverse to the catheter center axis 40 and the fluid flow. The distal tip wall 24 defines a second profile also substantially transverse to the catheter center axis 40 and the fluid flow. The second profile is greater in dimension than the first profile. Hence, this serves to promote fluid flow through the distal tip opening 38 and hence over the transducer 22.

To further promote fluid flow over the transducer 22, the transducer has a surface 22a over which the fluid flows that is disposed at an angle sloping toward the catheter center axis in the proximal direction. This presents a greater surface resistance against the fluid flow to assure fluid contact therewith.

FIG. 3 shows another imaging catheter 110 according to a further embodiment of the present invention. The catheter 110 is similar to the catheter 10 of FIGS. 1 and 2 and hence, reference characters for like elements are repeated in FIG. 3. To further assure that air bubble formation in the vicinity of the transducer 22 is prevented during rotational operation, and with additional reference to FIG. 3, the proximal extent of the distal housing 26 is constructed with aqua ducts 41 and 42. As shown in FIG. 3, one aqua duct directs fluid onto the transducer face 22 from the top of the proximal portion of the distal housing 26, while the other aqua duct 41 directs fluid onto the transducer face 22 from the side. Further, the aqua ducts are built into the proximal portion 26 of the distal housing 16 at an angle with respect to a line extending along the catheter drive shaft 43. This is shown in FIG. 3 with the angle theta being formed with the intersection of a line 43 extending parallel to the catheter drive shaft 13 and a line 44 extending through the center of one of the aqua ducts 41. Both aqua ducts 41 and 42 are constructed at such an angle such that the proximal side of each duct leads the distal side in the direction of rotation. This is shown in FIG. 3 with the clockwise direction of rotation (from the view looking distally along the catheter drive shaft 13) indicated by 45. Further, each side of each aqua duct is constructed with a small radius of curvature shown by 46 in FIG. 3. One way to achieve the duct side curvatures is to construct the ducts in a helical spiral with a small pitch, as, for example, on the order of 0.1 inch. The duct angle and curvature, coupled with rotation of the distal housing 16 and the fluid flow promoting structure shown in FIG. 1, act to continuously draw fluid residing within the catheter sheath 12, proximal to the distal housing 16, onto the face of the transducer 22. Fluid flow within the sheath from proximal to the transducer 22 to distal of the transducer 22 is conducted down the tapered cutout surface 26, over the transducer 22, and out the distal tip wall opening 38 in a continuous manner, without turbulence, to prevent air bubble formation in the vicinity of the transducer.

While particular embodiments of the present invention have been shown and described, modifications may be made, and it is therefore intended in the appended claims to cover all such changes and modifications which fall within the true spirit and scope of the invention as defined by those claims.

What is claimed is:

1. An imaging probe for use in a catheter for ultrasonic imaging, the catheter including a sheath having an opening at a distal end for conducting a fluid there through, the imaging probe comprising:
    a distal housing arranged to be received by the sheath and being coupled to a drive shaft for rotation to render the distal housing rotatable relative to the sheath;
    a transducer within the distal housing for generating and sensing ultrasonic waves, the transducer being rotatable along with the distal housing relative to the sheath; and
    a fluid flow promoter carried on the distal housing that promotes flow of the fluid within the sheath across the transducer and out the opening at the distal end of the sheath.

2. The imaging probe of claim 1, further including a wall distal to the transducer, and wherein the fluid flow promoter includes an opening within the wall and adjacent to the transducer.

3. The imaging probe of claim 2, wherein the distal housing has a first profile at a proximal end of the distal housing, a second profile at the wall distal to the transducer, and wherein the fluid flow promoter includes the second profile being greater than the first profile to promote fluid flow over the transducer and through the opening within the wall.

4. The imaging probe of claim 1, wherein the catheter has a center axis and wherein the fluid flow promoter further includes a mounting for the transducer that disposes the transducer at an angle sloping toward the catheter center axis in a proximal direction.

5. The imaging probe of claim 1, wherein the distal housing has a proximal extent and wherein the fluid flow promoter includes at least one aqua duct within the proximal extent of the distal housing.

6. The imaging probe of claim 5, wherein the catheter has a center axis and wherein the at least one aqua duct is formed within the proximal extent of the distal housing at an angle to the center axis.

7. The imaging probe of claim 5, wherein the at least one aqua duct comprises at least two aqua ducts.

8. The imaging probe of claim 7, wherein the transducer includes a face surface, wherein the at least two aqua ducts include a first aqua duct that directs fluid directly onto the face surface of the transducer, and wherein the at least two aqua ducts include a second aqua duct that directs fluid onto the face surface of the transducer from a side of the transducer.

9. The imaging probe of claim 5, where the at least one aqua duct has a proximal side and a distal side and wherein the at least one aqua duct is formed so that the proximal side leads the distal side in the direction of rotation of the distal housing.

10. The imaging probe of claim 5, where the at least one aqua duct includes a radius of curvature.

* * * * *